United States Patent [19]

Lee et al.

[11] 4,249,537

[45] Feb. 10, 1981

[54] CURRENT CONTROLLED MUSCLE STIMULATOR

[76] Inventors: Ronald L. Lee, 1001 Burning Springs Cir., Louisville, Ky. 40223; Charles G. Chaconas, 13801 Marianna Dr., Rockville, Md. 20853

[21] Appl. No.: 40,458

[22] Filed: May 18, 1979

[51] Int. Cl.$^3$ ............................................. A61N 1/36
[52] U.S. Cl. ................................... 128/422; 323/247; 330/196
[58] Field of Search ............ 128/419 R, 419 S, 420 R, 128/420 A, 421, 422, 423 R, 908; 323/6, 9; 330/122, 123, 196

[56] References Cited

U.S. PATENT DOCUMENTS

| | | | |
|---|---|---|---|
| 3,589,370 | 6/1971 | McDonald | 128/422 |
| 3,648,708 | 3/1972 | Haeri | 128/422 |
| 3,718,132 | 2/1973 | Holt et al. | 128/421 X |
| 3,817,254 | 6/1974 | Maurer | 128/421 |
| 3,835,833 | 9/1974 | Limoge | 128/422 X |
| 3,898,991 | 8/1975 | Ikuno et al. | 128/422 X |
| 4,019,519 | 8/1977 | Gearling | 128/422 |
| 4,102,348 | 7/1978 | Hihara et al. | 128/422 |
| 4,157,087 | 6/1979 | Miller et al. | 128/422 X |

*Primary Examiner*—Lee S. Cohen
*Attorney, Agent, or Firm*—Roylance, Abrams, Berdo & Farley

[57] ABSTRACT

An apparatus for stimulating and controlling the contraction of muscles includes conductive electrodes for contacting spaced-apart locations on the body between which are the muscles to be exercised. The electrodes are connected to a signal supply circuit which includes a pulse generator, a modulator circuit, a push-pull amplifier, a current control circuit and a transformer, the primary winding of which is driven by the amplifier and the secondary winding of which is connected to the electrodes. A second, lower repetition rate, pulse generator can be included to modulate the output so that signals are provided in spaced groups of pulses. The controlled current output is adjustable and monitored by a meter. A counter for counting pulse groups is included.

8 Claims, 5 Drawing Figures

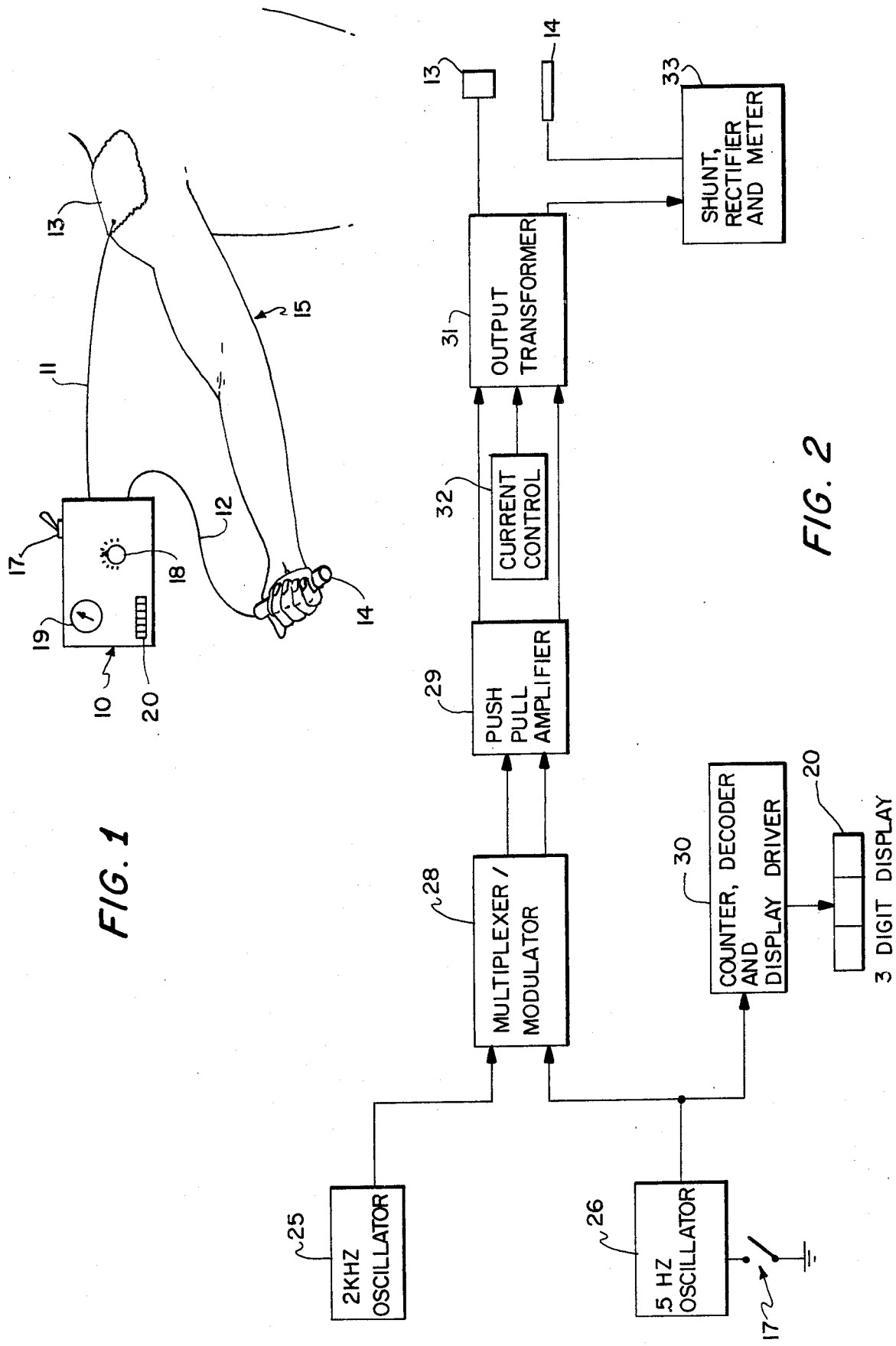

WAVE FORMS

CONTINUOUS MODE:

REPETITION MODE:

CURRENT CONTROLLED MUSCLE STIMULATOR

This invention relates to apparatus for applying electrical signals to a human, or other animal, body for muscle stimulation, and, in particular, to improved control apparatus thereof.

BACKGROUND OF THE INVENTION

It has been realized for quite some time that the muscles of a human or other animal are normally caused to contract in response to electrical signals generated in the body and that externally generated electrical signals can be applied to muscle tissue to induce contraction thereof. This phenomenon is familiar to students of biology in experiments following dissection, and the technique, broadly has been employed with cardiac muscle tissue and in other ways as illustrated by the following issued U.S. Pat. Nos.

3,472,233 Sarbacher;
3,566,877 Smith et al;
3,628,538 Vincent et al;
3,773,051 Holcomb et al;
3,881,496 Vredenbregt et al;
3,946,745 Hsiang-Lai et al;
3,978,864 Smith et al;
3,983,881 Wickham;
4,019,518 Maurer et al;
4,071,033 Nawracaj et al;

As recognized in Sarbacher, electrical pulses can be applied through electrode pads applied to the skin to stimulate muscle activity, and others of the above patents relate to implants and other forms of applying electrical energy to the body.

BRIEF DESCRIPTION OF THE INVENTION

As will be recognized, the application of electrical signals to the human body, or to the body of an animal, must be done with care to avoid the possibility of physiological damage, and yet it has been found that significant voltage must be available to overcome skin resistance. It has also been recognized that the skin resistance of an individual varies from time to time and that there is some variation therein between individuals. Thus, if one simply provides a device which is capable of producing a very low voltage, or low power, signal, safety will be achieved at the expense of effectiveness.

It has also been found that some variation in current level is necessary to stimulate various sets of muscles because of differences in size and characteristics thereof.

An object of the present invention is to provide an improved apparatus for applying, and safely controlling the application of, electrical energy to the body through electrodes contacting the skin, for stimulating muscle activity.

A further object is to provide control circuitry for the application of pulse energy such that the electrical current is limited to a safe level while permitting the voltage to vary as a function of individual skin resistance.

Yet another object is to provide a control circuit for the above purposes which permits operation in two modes and which permits control of the level of current applied to the the body, and which provides displays to permit an operator to be aware of characteristics of the signals applied.

Briefly described, the invention includes an improved apparatus for producing and applying controlled muscle-stimulating electrical signals to the body, the apparatus being of the type having a pair of electrically conductive electrode means for contacting the body and conducting electricity thereto, a source of electrical energy, pulse circuit means connected to the source of energy for producing electrical pulses, and conductor means for coupling the pulses to the electrode means, the improvement comprising current control means in said pulse circuit means for limiting the average level of current supplied to said conductor means to a predetermined level substantially independently of voltage.

The pulse circuit means preferably includes pulse generators for producing trains of pulses at two significantly different repetition rates, the generator producing signals at a lower rate being selectively energizable by use of a mode switch. A multiplexer or modulator circuit receives the outputs of the two pulse generators and, when the lower repetition rate generator is not energized, continuously produces two signal outputs in phase opposition to drive a push-pull amplifier which is coupled to the muscle-stimulating electrodes. When the lower repetition rate generator is activated, the modulator output consists of the trains of pulses only when the low-rate generator is producing a signal at one level, the output at the other level being zero.

In order that the manner in which the foregoing and other objects are attained in accordance with the invention can be understood in detail, particularly advantageous embodiments thereof will be described with reference to the accompanying drawings, which form a part of this specification, and wherein:

FIG. 1 is a schematic illustration of an apparatus in accordance with the invention showing one use thereof;

FIG. 2 is a schematic diagram, in block form, of a control circuit in accordance with the invention;

Figure 3:
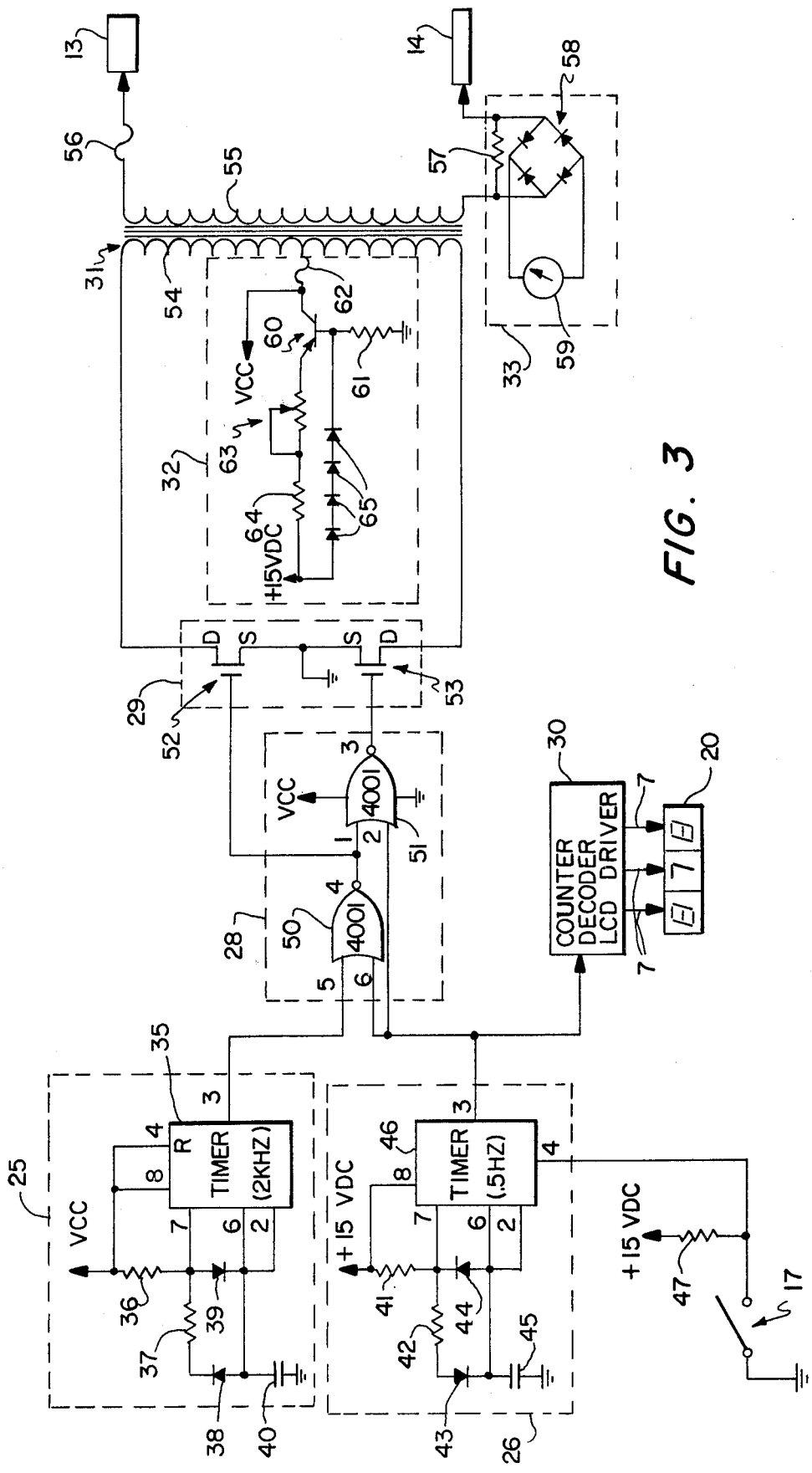
FIG. 3 is a more detailed schematic diagram, still partly in block form, of the control circuit usable in the apparatus of FIG. 1.

Before discussing the drawings in detail, it should be noted that the present invention has substantial utility in various medical and therapeutic applications, the general purpose being to provide a technique for exercising selected muscles or muscle groups using electrical stimulation. It will be apparent that such exercising is particularly useful with individuals not capable of independently engaging in normal exercise routines, examples of such situations being in individuals with medical disorders preventing them from activating muscles or muscle groups without assistance. No effort will be made herein to engage in a discussion of the medical conditions which might give rise to the circumstances, but it will be apparent that various medical conditions result in limited or complete muscle inactivity and that a failure to stimulate the muscles can result in varying degrees of muscle atrophy. Appropriate use of an apparatus in accordance with the invention can, by proper exercise, significantly reduce the adverse effects of such a condition.

For this purpose, it is desirable to contract and relax various muscles, and the sequencing and control thereof can be easily accomplished using the control system disclosed herein.

Referring now to FIG. 1, the apparatus includes a control unit indicated generally at 10 having electrical conductors 11 and 12 connected respectively to electrodes 13 and 14 which are applied to a body, either human or animal. For purposes of example, an arm 15 is illustrated with one electrode 13 being placed on the deltoid muscle at the shoulder and the other electrode 14 being held in the hand. The electrodes themselves can be moistened pads of fabric or, as illustrated at 14, a rod of metal surrounded by a moistened pad which is held in the hand. The pads can be any conventional fabric capable of absorbing fluids, and the moistening fluid is advantageously a saline solution. It will be assumed that the object of the exercise is to stimulate activity in the bicep, tricep or forearm muscles. The control unit includes external indicators and controls such as a mode switch 17, a current level control adjustment, 18, a current level indicating meter 19 and a repetition counter 20, the individual functions of which will be described more fully hereinafter.

Basically, the apparatus is utilized by placing the electrodes at locations on the body between which lie the muscles or muscle groups of interest and by then energizing the apparatus with the current control set at a low level. The current is then increased gradually while observing the subject and the current level indicator. The effect of the current on the subject will be readily apparent as muscles contract, moving the affected portion of the body as the contraction occurs. The action of the muscles under these conditions is completely beyond the control of the subject, regardless of the amount of independent control of those muscles which the subject is capable of exercising in the absence of external electrical stimulation. In the situation shown, as current is caused to increase, the forearm muscles will first contract, then the bicep muscles and then the triceps, causing the hand and then the forearm to flex and then extend. The current levels are relatively low, measured in relatively few milliamperes, and should be maintained within safe limits specified by the American National Standard Safe Current Limits for Electromedical Apparatus, publication ANSI/AAMI, SCL12/78, published by the Association for the Advancement of Medical Instrumentation located in Arlington, Virginia.

FIG. 2 shows a block diagram of the control apparatus 10 connected to electrodes 13 and 14. The control apparatus includes a first pulse generator circuit 25 which is advantageously designed to produce a train of unidirectional pulses at a repetition rate of approximate 2 kilohertz. A second pulse generator circuit 26 of a substantially identical nature is designed to produce pulses at a rate of 0.5 Hertz, significantly lower than the repetition rate of generator 25. For convenience, these circuits can be thought of as substantially constant frequency oscillators. Oscillator 26 is connected to mode switch 17, the function of the mode switch being to permit selective energization or deenergization of the lower repetition rate oscillator.

The outputs of oscillators 25 and 26 are connected to the inputs of a multiplexer/modulator circuit 28 which produces two pulse train outputs to the inputs of a push-pull amplifier circuit 29. The output of oscillator 26 is also connected to a counter and decoder circuit 30 which drives digital display 20, to be subsequently described.

The two outputs of amplifier 29 are connected to the ends of a primary winding of an output transformer 31 to which a current control unit 32 is connected. The output winding of the transformer is connected to the electrodes, one end of the winding being connected to electrode 13 and the other end of the winding being connected, through a shunt, rectifier and meter circuit 33, to electrode 14. As will be described, circuit 33 includes meter 19 and is for the purpose of indicating the level of current being supplied to the electrodes and the body of the subject The multiplexer/modulator circuit performs two basic functions. In one operational mode, which will be referred to as the continuous mode, oscillator 26 is de-energized and circuit 28 is supplied with pulses at 2 kHz. The output from circuit 28 consists of two pulse trains to the push-pull amplifier, each pulse train being a series of pulses at a repetition rate of 2 kHz, one of the pulse trains being displaced in phase from the other by 180° or, stated differently, the two pulse trains are in phase opposition. This output is supplied continuously, as long as the overall apparatus is energized. The push-pull amplifier output therefore consists of two substantially identical, but phase shifted outputs which drive opposite ends of a center-tapped primary winding, thereby alternately driving the output from the secondary winding in opposite directions.

In the other mode, which will be referred to as the repetition mode, switch 17 is opened and oscillator 26 is in operation. In this mode, the logic within circuit 28 is selected such that during one-half of each cycle of the output of oscillator 26, circuit 28 produces no output; and during the other half cycle, the output is identical to the output which occurs in the continuous mode. The push-pull amplifier and the output transformer thus supply a burst of pulses followed by an interval of no output, again followed by a burst of pulses. This sequence continues for as long as the apparatus is energized and switch 17 is opened. With a repetition rate of 0.5 Hz for oscillator 26, the on and off sequence occurs in cycles of two seconds each, thus providing an output for one second and an interval of one second with no output.

FIG. 3 shows in somewhat more detail the manner in which the foregoing is accomplished. Each of oscillators 25 and 26 includes substantially identical components insofar as a schematic diagram is concerned, the only differences between these circuits being the values of the circuit components. Circuit 25 includes a timer which can be a conventional commercially available integrated circuit timer such as the NE555N manufactured by Signetics Corp., Sunnyvale, Calif. Other similar chips can be used, this particular one having a bistable circuit, comparators, and an output stage capable of driving cmos logic. In circuit 25, timer 35 has its supply and reset terminals 8 and 4 connected to a supply source which, for this specific chip, is 15 volts. The discharge terminal 7 of the timer is connected to a resistor 36 and a resistor 37, the other end of resistor 36 being connected to the supply terminal and the other end of resistor 37 being connected to the anode of a conventional diode 38 which can be a standard signal diode such as a 1N3067. The junction between resistors 36 and 37 is also connected to the cathode of a diode 39 of the same type, the other ends of these diodes being connected to each other, to the threshold terminal 6 and the trigger terminal 2 of the timer, and to one terminal of a capacitor 40, the other terminal of which is connected to ground. The output terminal 3 of the timer is connected to one input of circuit 28.

The circuit configuration for pulse generator 26 is identical, with one exception, to the circuit for generator 25, circuit 26 including resistors 41 and 42 and a capacitor 45, the diodes 43 and 44 being of the same type. The one exception is that the reset terminal for timer 46 in circuit 26 is connected to switch 17 and to one terminal of a resistor 47, the other terminal of which is connected to a positive DC source.

In circuit 25, when an NE555N chip is employed, for a repetition rate of 2 kHz, resistors 36 and 37 are 10,000 Ohms each and capacitor 40 has a value of 0.022 microfarads. In circuit 26, for a repetition rate of 0.5 Hz, resistors 41 and 42 each have a value of 1 megohm and capacitor 45 has a value of 1 microfarad. Resistor 47 has a value of 47,000 Ohms.

The multiplexer/modulator circuit 28 is a relatively simple circuit including two inverting OR circuits 50 and 51, each of which can be a type 4001 circuit which is readily available in multiple packages. One input of each of circuits 50 and 51 is connected to the output terminal 3 of timer 46. The other input of circuit 50 is connected to the output of timer 35, the output of circuit 50 being connected to the input of circuit 51 and to one of the inputs of push-pull amplifier 29. The output of circuit 51 is connected to the other input of the push-pull amplifier.

The push-pull amplifier is also a relatively simple circuit including two field effect transistors indicated at 52 and 53, the inputs being the gates of these FET's. Each FET can be a S75V02. The source electrode of each FET is connected to ground and the drain electrode is connected to one end of the primary winding 54 of output transformer 31. It will be observed that winding 31 is center-tapped and that the center tap is connected to current control circuit 32. Secondary winding 55 of transformer 31 is connected through a fuse 56 to electrode 13 and through circuit 33 to electrode 14. Circuit 33 includes a shunt resistor 57 which is in series between winding 55 and electrode 14. A conventional bridge rectifier circuit 58 is connected across resistor 57 and a DC meter 59 is connected across the output terminals of the bridge rectifier. As will be readily recognized, the voltage across resistor 57 is proportional to the current therethrough and the output of the bridge, displayed on meter 59, is therefore proportional to that current.

Current control circuit 32, which is a particularly significant aspect of the apparatus, includes a conventional PNP resistor indicated at 60 having its base electrode connected through a resistor 61 to ground, its collector electrode connected through a fuse 62 to the center tap of winding 54, and its emitter electrode connected to one end of a 25 Ohm potentiometer 63. The other end of potentiometer 63 is connected through a fixed resistor 64 to the positive DC supply, resistor 64 having a value of 2.7 Ohms. A series circuit including four diodes 65 is connected between the positive supply and the base electrode of transistor 60. These diodes can also be type 1N3067 diodes as used in circuits 25 and 26.

It will be observed that the supply to FET's 52 and 53 in amplifier 29 is through current control circuit 32 and the transformer primary. Thus, transistor 60 and its associated components regulate the current to the push-pull amplifier, thus regulating the AC output current therefrom. When the 25 ohm potentiometer is adjusted so that the movable wiper thereof is to the left, placing its full resistance in series with the transistor, a resistance of 27.7 ohms exists between the 15-volt supply and the emitter of transistor 60. The series diodes cause the base of transistor 60 to be 2.8 volts below the 15-volt supply, or at 12.2 volts. The diode drop of the emitter-base junction of transistor 60 places the transistor emitter at 12.9 volts. Thus, the current through the circuit is established at (15-12.9)/27.7 which equals 75 milliamperes. This current level does not provide enough power to allow the system to operate and constitutes the zero output current, or cut-off, mode of operation. As the movable wiper of the potentiometer is adjusted to the right, the current level rises. At the maximum level, the total resistance in the circuit is at 2.7 ohms, the value of resistor 64, and the current reaches a maximum of 777 milliamperes. Using a transformer having a ratio of 24:117, or a ratio of 0.205, it will be recognized that the ratio of the transformer output current to the transformer input current will also be 0.205. Thus, using a practical maximum input current of 700 milliamperes, allowing for efficiency of the transformer and current losses in other portions of the system, the output current will be about 144 milliamperes. If the transformer is 70% efficient, the effective output current will be 100 milliamperes. This level of current will ensure active muscle stimulation.

For safety purposes, fuse 62 is preferably a 0.75 ampere fuse and fuse 56 is a 0.1 ampere fuse, these being provided to guarantee that no greater current level is reached.

Shunt resistor 57 and the full-wave rectifier are used to calibrate the meter movement so that a full scale reading on the meter is reached at a 100 milliampere output. This calibration is accomplished in a conventional fashion.

Figure 4:
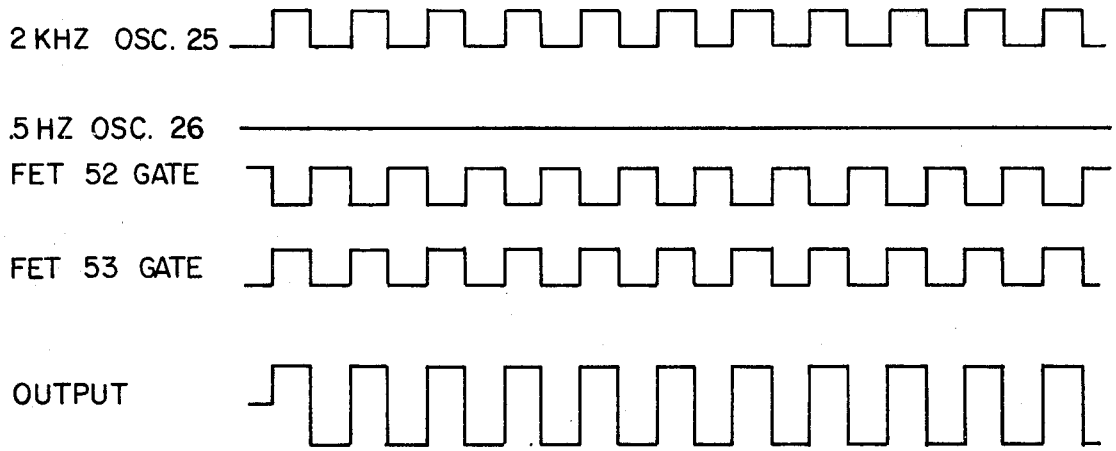
FIGS. 4 and 5 are wave form diagrams showing the relationship between pulses appearing in the circuit of FIG. 3 in the continuous and repetition modes, respectively.
Figure 5:
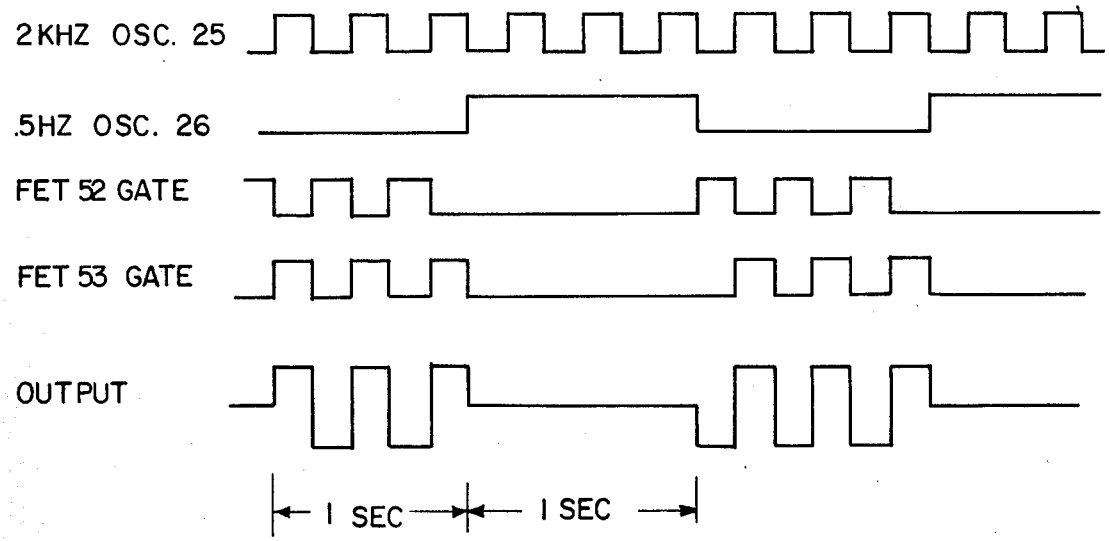

FIGS. 4 and 5 illustrate the two modes of operation of the apparatus. In the continuous mode illustrated in FIG. 4, the output of oscillator 25 is illustrated as the top line of FIG. 4, the square wave illustrated being indicative of the output of that oscillator but shown at a somewhat lower frequency for simplification of illustration. The second line of FIG. 4 is the output of oscillator 26 which, in the continuous mode, is zero. In this mode, the outputs of circuit 28, which constitute the inputs to FET amplifiers 52 and 53, are illustrated as the third and fourth lines of FIG. 4, these constituting square waves in phase opposition. The output of transformer 31 is shown as the bottom line of FIG. 4 although it will be recognized that the output at that stage will not normally constitute a pure square wave because of normal transformer distortion.

In the repetition mode illustrated in FIG. 5, the wave forms are taken at the same points in FIG. 4. As will be seen, the output of oscillator 26 is active and produces a high level for one-half of each of its 0.5 Hz cycles. During that interval, the signals from inverting OR gates 50 and 51 are blocked and the outputs therefrom are forced to a low level. Thus, the inputs to the gates of FET's 52 and 53 are zero, and the output from transformer is also zero. When the output of oscillator 26 is low, the operation of the circuits is identical to that in FIG. 4. This permits a one second on and one second off alternating repetition of energy to the muscle causing alternate contraction and relaxation thereof.

The counter circuit 30 can optionally be used to keep track of the number of contractions which occur during operation of oscillator 26 in the repetition mode. Circuit 30 is a conventional counter, decode and LCD driver and can be constructed of individual integrated circuit or, more preferably, can be found in a single integrated circuit device. Such a device is completely conventional and will not be further described. The outputs, which consist of sets of seven outputs to drive a conventional seven-segment display, are provided to display 20 which simply shows a count of contraction cycles.

As will be recognized, with the effective current-limiting action shown and described, the current applied to the subject results in safe and smooth muscle stimulation. Also, with this current regulation, no change in the stimulation level will be experienced even though the electrical resistance of the patient, due to skin resistance or other factors, changes as a result of exercise, perspiration, fatigue, or other factors. On the other hand, the voltage can change within a relatively wide range of values to overcome high skin resistance, where necessary.

While certain advantageous embodiments have been chosen to illustrate the invention, it will be understood by those skilled in the art that various changes and modifications can be made therein without departing from the scope of the invention as defined in the appended claims.

What is claimed is:

1. An improved apparatus for producing and applying controlled muscle-stimulating electrical signals to the body, the apparatus being of the type having a pair of electrically conductive electrode means for contacting the body and conducting electricity thereto, a source of electrical energy, pulse circuit means connected to the source of energy for producing electrical pulses, and conductor means for coupling the pulses to the electrode means, the improvement wherein
   said pulse circuit means includes an output transformer having a center-tapped primary winding and a secondary winding, said secondary winding being connected through said conductor means to said electrode means;
   said apparatus further including current control means in said pulse circuit means for limiting the average level of current supplied to said conductor means to a predetermined level substantially independently of voltage;
   and wherein said current control means includes a constant current circuit connected between said center tap and a point of reference potential, and means for adjusting the current control level of said constant current circuit.

2. An apparatus according to claim 1 wherein said pulse circuit means includes
   first and second oscillator circuit means for producing a series of pulses at first and second repetition rates, respectively;
   modulator circuit means connected to receive the pulse outputs of said first and second oscillator circuit means for producing first and second output signals; and
   a push-pull amplifier having input terminals connected to receive said first and second output signals and output terminals connected to opposite ends of said primary winding.

3. An apparatus according to claim 2 and further comprising
   circuit means coupled to said secondary winding for producing a signal representative of the current passing therethrough; and
   display means for indicating the magnitude of said current.

4. An apparatus according to claim 2 wherein the repetition rate of the pulses produced by said first oscillator circuit means is in the order of 4,000 times greater than the rate of said second oscillator circuit means; and wherein said modulator circuit means is responsive to said series of pulses to produce first and second output signals each consisting of pulses at the repetition rate of said first oscillator circuit means, the pulses in the first output signal being separated in phase from those in the second output signal by 180°, said output signals being produced during only one-half of each cycle of the output of said second oscillator circuit means.

5. An apparatus according to claim 4 and further comprising a mode switch connected between said source of energy and said second oscillator circuit means for selectively energizing and deenergizing said second oscillator circuit means.

6. An apparatus according to claim 5 and further comprising
   counter circuit means connected to said second oscillator circuit means for accumulating a count of pulses produced thereby; and
   means for displaying said count.

7. An apparatus according to claim 1 wherein said pulse circuit means further comprises
   first pulse generator circuit means for producing pulses at a first repetition rate;
   second pulse generator circuit means for producing pulses at a second repetition rate which is significantly lower than said first repetition rate;
   manually operable switch means for selectively activating said second pulse generator circuit means, and
   logic circuit means connected to the outputs of said first and second pulse generator circuit means and having two output terminals for producing two output signals consisting of pulse trains in phase opposition at said first repetition rate when the output of said second pulse generator circuit means is at one level and for producing no output signal when the output of said second pulse generator circuit means is at the other level.

8. An apparatus according to claim 7 and further comprising
   a push-pull amplifier circuit having input terminals connected to the output terminals of said logic circuit means and output terminals connected to opposite ends of said primary winding.

* * * * *